United States Patent [19]

Bowden

[11] Patent Number: 4,546,318

[45] Date of Patent: Oct. 8, 1985

[54] METHOD FOR REGULATING CURRENT FLOW THROUGH CORE SAMPLES

[75] Inventor: Edgar A. Bowden, Arlington, Tex.

[73] Assignee: Mobil Oil Corporation, New York, N.Y.

[21] Appl. No.: 478,190

[22] Filed: Mar. 11, 1983

[51] Int. Cl.[4] .................... G01R 27/08; G01N 27/04; G01V 3/06; G05F 1/12

[52] U.S. Cl. .................... 324/376; 323/280; 324/64

[58] Field of Search .................. 324/376, 357, 64, 442, 324/444; 323/280, 312; 307/297

[56] References Cited

U.S. PATENT DOCUMENTS

| | | | |
|---|---|---|---|
| 2,793,292 | 5/1957 | Wolff | 324/64 X |
| 2,871,446 | 1/1959 | Wann | 324/64 |
| 2,988,690 | 6/1961 | Love et al. | 324/357 |
| 3,895,289 | 7/1975 | Rickey et al. | 324/323 |
| 3,946,309 | 3/1976 | Roughton et al. | 324/64 |
| 3,988,669 | 10/1976 | Fasching | 324/64 X |
| 4,281,289 | 7/1981 | Donaldson et al. | 324/376 X |
| 4,302,726 | 11/1981 | Shobbrook | 323/280 X |

OTHER PUBLICATIONS

Frederiksen et al.; "Diode-feedback ... regulates a LED's drive current", *Electronic Design* 6, vol. 25, Mar. 15, 1977, p. 108.

Sarma et al.; IR compensation in potentiostat, *Electroanalytical Chem. and Interfacial Electrochem.*, 41, No. 3, Feb. 9, 1973, pp. 503, 504.

*Primary Examiner*—Gerard R. Strecker
*Attorney, Agent, or Firm*—A. J. McKillop; Michael G. Gilman; George W. Hager, Jr.

[57] ABSTRACT

A method and system for regulating current flow through a core sample from a subterranean formation being tested for electrical impedance, including a variable-frequency current source, means for passing such current through the core sample, means for measuring such current flow, and means for regulating the current flow through the core sample so that it is dependent upon the amplitude of the current flow from the current source and is independent of non-linear variations in core inpedance responsive to the current flow through the core sample.

1 Claim, 2 Drawing Figures

METHOD FOR REGULATING CURRENT FLOW THROUGH CORE SAMPLES

BACKGROUND OF THE INVENTION

This invention relates to a method and system for applying a stimulating current flow to core samples taken from subterranean formations and relates more particularly to a method and system for regulating the stimulating current flow through core samples having non-linear properties.

In the drilling of wells, such as oil or gas wells, cores are taken of the earth strata through which the wells are drilled and various characteristics of the cores or core samples are determined for the purpose of establishing fluid in the strata, estimating the quantity of fluid in the strata, the ease of flow through the strata, etc. Such core samples are also taken from producing strata and characteristics of the core samples are determined for the purpose of estimating fluid reserves, predicting production rates, etc. Among the characteristics of core samples commonly determined is the formation resistivity factor involving the measurement of the electrical resistivity of the core samples.

However, previous methods for measuring electrical resistivity of core samples have failed to take into account certain factors which affect the resistivity measurements. It has been found that core samples of earth material may exhibit nonlinear properties. When a core sample with such non-linear properties is stimulated with a sine wave its response is distorted from a sine wave response. This distorted response is due to the fact that at some current density there is a threshold for inducing an electro-chemical reaction. It is therefore an object of the present invention to overcome such a non-linearity factor in the measurement of the electrical resistivity of core samples.

SUMMARY OF THE INVENTION

The present invention is directed to apparatus for regulating current flow through core samples from subterranean formations being tested for electrical impedance. An oscillator supplies a current flow to a core sample through a current regulator. The current regulator controls the current flow through the core sample such that the core current is directly proportional to the oscillator voltage and independent of non-linearities in the core.

More particularly, a series resistance is connected between the oscillator and the core sample. A current detector provides an analog representation of the amplitude of the current flow through the series resistance. The current regulator compares the analog representation of the current flow through the series resistance with the current flow from the oscillator and operates to hold the difference between the magnitudes of such current flows to zero.

DESCRIPTION OF THE PREFERRED EMBODIMENT

Figure 1:
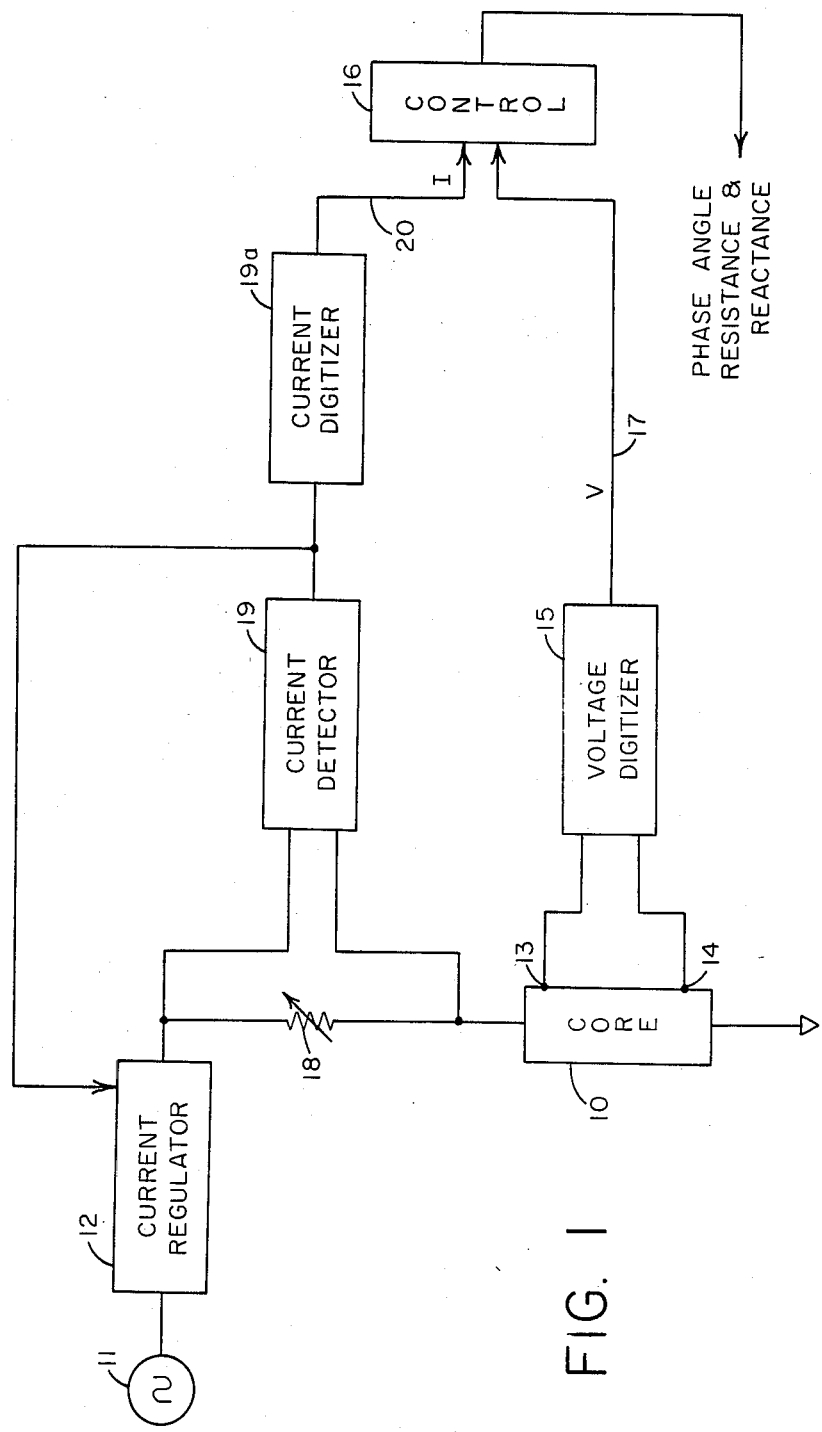
FIG. 1 illustrates a block diagram schematic of the core sample testing apparatus of the present invention.

Referring now to FIG. 1 there is illustrated a core sample 10 to be tested for electrical resistivity. Stimulating current for passing through core sample 10, in order to carry out resistivity or impedance testing, is supplied by an oscillator 11 and a current regulator 12. A variable-frequency current source 11 of from 0.001 hertz to 25 kilohertz, for example, is connected to the current regulator 12. The regulator applies a stimulating current flow through the series resistor 18 to the core sample 10. The current is regulated against non-linear core loads. This regulated current flow is totally dependent upon the amplitude of the current waveform from the current source, that is, independent of variations in the core impedance.

The resulting voltage drop across the core is measured at terminals 13 and 14 which are located away from the ends of the core so as to eliminate possible electrochemical errors resulting from the current input and output connections to the core. This voltage drop is amplified and operated upon by the voltage digitizer 15 to produce a digitized voltage signal V on line 17.

The current through the core is measured across the resistor 18 by current detector 19 and digitized by current digitizer 19a to produce the digitized current signal I on line 20. Both this current signal I and the voltage signal V are applied to a control unit 16 which operates to determine, among other things, the phase angle of the measured current with respect to the measured voltage. By thus having a measure of the voltage across the core, the current thorugh the core, and the phase angle between such voltage and current, the correct electrical resistance and reactance of the core sample can be determined.

Figure 2:
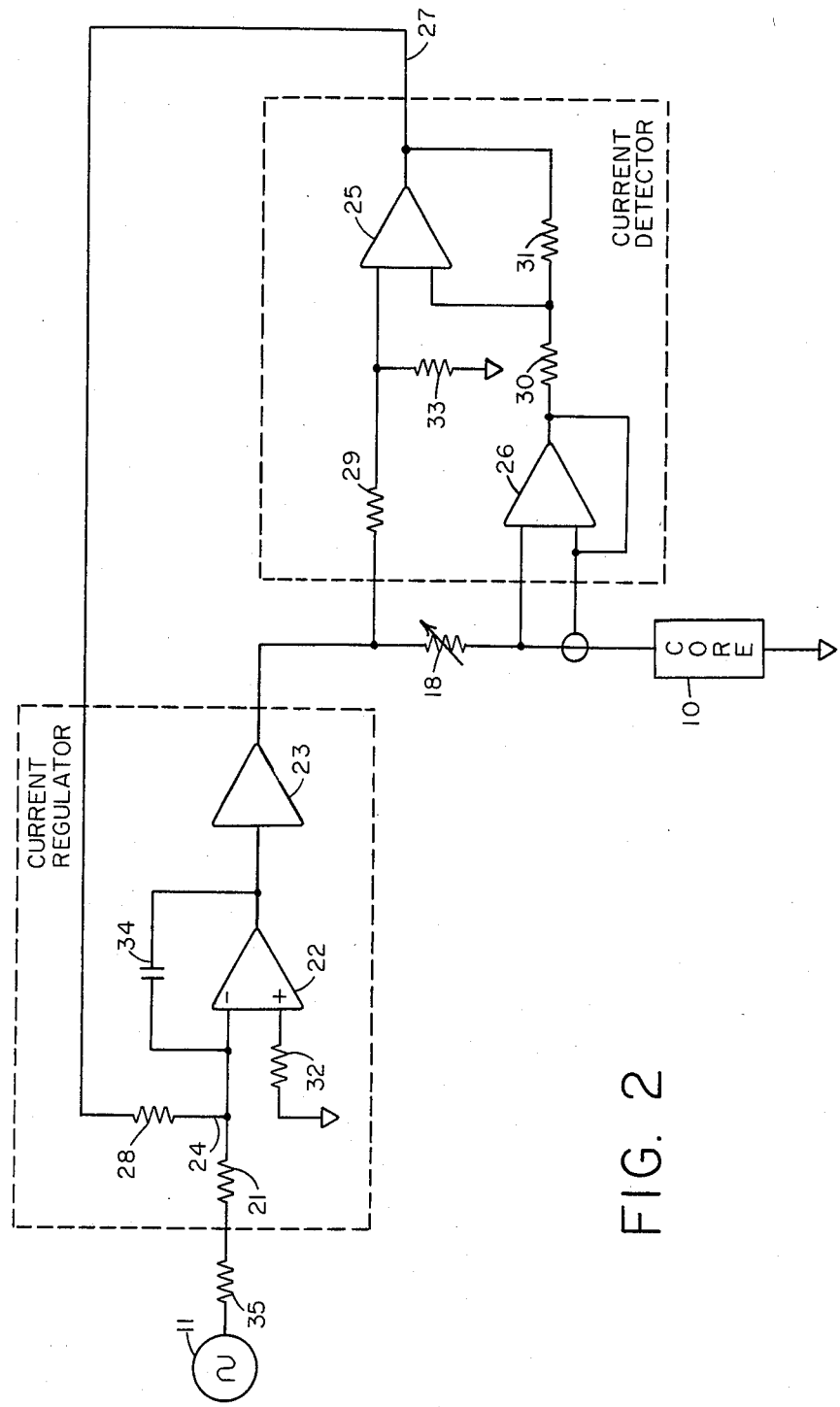
FIG. 2 is an electrical circuit schematic of the current detector and current regulator of the apparatus of FIG. 1.

Referring now to FIG. 2, there is illustrated the current regulator 12, the resistor 18 and the current detector 19 of FIG. 1.

The variable frequency oscillator 11 is connected through input resistance 21 to the inverting input of the summing amplifier 22 where it is summed with the analog current on line 24 as will be more fully expalined later. The summed signal from amplifier 22 is applied through the driver 23 to the series resistor 18 and the core sample 10. The voltage across resistor 18 is measured by the amplifier combination 25 and 26, amplifier 25 functioning as a differential amplifier and amplifier 26 functioning as a buffer amplifier. The output of amplifier 25 on line 27 is an analog representative of the stimulation current flow through the source resistor 18 to the core sample 10.

This output from amplifier 25 is applied by way of line 27, resistor 28, and line 24 to the inverting input of amplifier 22 to be summed with the current input from the oscillator 11. Amplifier 22 operates to hold the difference between the magnitude of the current flows through resistors 21 and 28 to zero, that is, it operates to equalize the magnitude of the current flows from the oscillator 11 and through the core 10. In this manner the stimulating current flow through the core 10 is regulated to always be proportional to the amplitude of the oscillator current independent of any non-linear response of the core sample which would otherwise distort the sine wave of the stimulating current through electro-chemical reaction.

Having described the method and system of the present invention in conjunction with the circuitry illustrated in FIGS. 1 and 2, it is to be understood that such circuitry is merely representative of one embodiment. In accordance with such embodiment, the following sets forth specific types of circuit components.

| Reference Designation | Description |
| --- | --- |
| Oscillator 11 | HP 3325 (Hewlett Packard) |
| Summing Amplifier 22 | OP15 (Precision Monolithics Inc.) |
| Driver Amplifier 23 | LH0002 |
| Differential Amplifier 25 | OP15 (Precision Monolithics Inc.) |
| Buffer Amplifier 26 | OP15 (Precision Monolithics Inc.) |
| Resistor 21 | 1 kilohm |
| Resistor 28 | 10 kilohms |
| Resistors 29-32 | 4.99 kilohms |
| Resistor 35 | 4.22 kilohms |
| Resistor 33 | 49.9 kilohms |
| Capacitor 34 | 470 picofarads |

It is to be understood that the foregoing description relates to only a preferred embodiment of the invention and that modifications or alterations may be made without departing frm the spirit and scope of the invention as set forth in the appended claims.

I claim:

1. A method for regulating current flow through a core sample having a non-linear response to such current flow due to electro-chemical reaction between the non-linear core sample and the current flow, comprising:
   (a) supplying current flow having a sine wave characteristic to said non-linear core sample to be tested for its electrical impedance,
   (b) connecting a resistance in series with said non-linear core sample,
   (c) measuring the distorted sine wave characteristic of the current flow through said resistance and said non-linear core sample caused by said electro-chemical reaction,
   (d) producing an analog signal representative of said distorted sine wave current flow,
   (e) applying said current flow having a sine wave chracteristic to the inverting input of a summing amplifier, and
   (f) applying said analog signal representative of the distorted sine wave current flow through said resistance and said non-linear core sample to the inverting input of said summing amplifier, said summing amplifier operating to regulate the current flow through said resistance and said non-linear core sample to be proportional to the sine wave characteristic of the current flow in the presence of said distortion caused by the electro-chemical reaction between said current flow and said non-linear core sample.

* * * * *